US006786919B1

(12) United States Patent
Escano et al.

(10) Patent No.: US 6,786,919 B1
(45) Date of Patent: Sep. 7, 2004

(54) SELF-EXPANDING INTRAVASCULAR DEVICE WITH PROTECTOR MEMBERS

(75) Inventors: Arnold M. Escano, Santa Clara, CA (US); Shuji Uemura, San Francisco, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/901,993

(22) Filed: Jul. 10, 2001

(51) Int. Cl.[7] ................................................. A61F 2/06
(52) U.S. Cl. ...................... 623/1.13; 623/1.53; 606/194
(58) Field of Search ............................. 623/1.13, 1.15, 623/1.32, 1.34, 1.36, 1.53, 1.16; 606/191, 194, 195, 198; A61F 2/06, 2/04

(56) References Cited

U.S. PATENT DOCUMENTS

| 5,304,200 A | | 4/1994 | Spaulding | |
|---|---|---|---|---|
| 5,383,892 A | * | 1/1995 | Cardon et al. .............. | 623/1.16 |
| 5,405,377 A | | 4/1995 | Cragg | |
| 5,443,499 A | | 8/1995 | Schmitt | |
| 5,476,508 A | | 12/1995 | Amstrup | |
| 5,503,636 A | | 4/1996 | Schmitt et al. | |
| 5,522,881 A | * | 6/1996 | Lentz ......................... | 623/1.13 |
| 5,545,208 A | | 8/1996 | Wolff et al. | |
| 5,630,829 A | * | 5/1997 | Lauterjung .................. | 606/198 |
| 5,667,523 A | * | 9/1997 | Bynon et al. ............... | 623/1.13 |
| 5,693,085 A | * | 12/1997 | Buirge et al. .............. | 623/1.13 |
| 5,733,328 A | * | 3/1998 | Fordenbacher ............. | 623/1.16 |
| 5,735,872 A | * | 4/1998 | Carpenter et al. .......... | 623/1.16 |
| 5,824,043 A | | 10/1998 | Cottone, Jr. | |
| 5,876,449 A | | 3/1999 | Starck et al. | |
| 5,899,935 A | | 5/1999 | Ding | |
| 6,010,529 A | * | 1/2000 | Herwerck et al. .......... | 623/1.13 |
| 6,013,093 A | * | 1/2000 | Nott et al. ................... | 606/200 |
| 6,033,436 A | * | 3/2000 | Steinke et al. ............. | 623/1.15 |
| 6,086,611 A | * | 7/2000 | Duffy et al. ................ | 623/1.13 |
| 6,123,723 A | * | 9/2000 | Konya et al. ............... | 623/1.11 |
| 6,143,022 A | * | 11/2000 | Shull et al. ................. | 623/1.13 |
| 6,197,049 B1 | * | 3/2001 | Shaolian et al. ........... | 623/1.35 |
| 6,203,568 B1 | * | 3/2001 | Lombardi et al. .......... | 623/1.13 |
| 6,221,079 B1 | * | 4/2001 | Magovern et al. .......... | 606/108 |
| 6,235,054 B1 | * | 5/2001 | Berg et al. ................. | 623/1.36 |
| 6,569,191 B1 | * | 5/2003 | Hogan ........................ | 623/1.11 |
| 6,589,275 B1 | * | 7/2003 | Ivancev et al. ............. | 623/1.15 |
| 6,623,521 B2 | * | 9/2003 | Steinke et al. ............. | 623/1.16 |
| 6,626,936 B2 | * | 9/2003 | Stinson ...................... | 623/1.15 |
| 2002/0173839 A1 | * | 11/2002 | Leopold et al. ............ | 623/1.15 |

FOREIGN PATENT DOCUMENTS

WO    WO 99/51165    * 10/1999 ............. A61F/2/06

* cited by examiner

Primary Examiner—David H. Willse
Assistant Examiner—Javier G. Blanco
(74) Attorney, Agent, or Firm—Fulwider Patton Lee & Utecht, LLP

(57) ABSTRACT

Protector elements for use in combination with medical devices configured to repair vasculature or other body lumens. In one aspect, the protector elements embody a cuff which provides a medical device with atraumatic surface and a desirable profile. In another aspect, the protector elements provide a medical device with enhanced structural integrity.

19 Claims, 3 Drawing Sheets

SELF-EXPANDING INTRAVASCULAR DEVICE WITH PROTECTOR MEMBERS

BACKGROUND OF THE INVENTION

The present invention relates to devices for repairing body lumens and more particularly, to self-expanding braided or mesh devices for support or repair of vasculature.

The vasculature of an animal or a human characteristically suffers from a variety of maladies. Vessel walls can weaken and become distended over time in response to blood flow and pressures, thereby resulting in formation of aneurysms. Such aneurysms can take on a myriad of forms. In particular, aneurysms may form at or near bifurcated vessels creating enlarged areas about the bifurcation, or may form a pocket, for example, in side walls of vessels. Due to the complications associated with aneurysms that rupture or otherwise fail, it is critical that an aneurysm be treated expeditiously and effectively. Intravascular treatment procedures include placing grafts within the aneurysm in a manner to ensure that blood flows through the graft rather than through the weakened vessel.

Stenoses also typically form in vasculature of humans and animals. Specifically, thrombotic or atherotic stenoses can form nearly anywhere in the vasculature. Such narrowing of the vessel is, of course, highly dangerous to the patient where the afflicted vessel provides the sole blood flow access to critical parts of the body. To treat such stenoses, a supporting structure can be placed at the diseased site for the purpose of enlarging and holding open the vessel. It is known in the art to employ stents for this purpose.

Vessel occlusions can also be treated by employing devices which are actuated to debulk and remove vessel occluding thrombi. This procedure is generally referred to as a thrombectomy. Typically, such devices are intravascularly advanced to the repair site and manipulated to remove the unwanted material from the vessel by physically engaging the thrombus and severing the same from the vessel wall.

Due to procedures such as thrombectomies or due to the natural, albeit undesirable, function of a patient's vasculature, emboli may be found traveling through a blood vessel. Embolic material can cause unwanted blockages or otherwise facilitate the formation of an occlusion in a vessel which too, can be highly dangerous to a patient. To address this problem, emboli-catching filters can be intravascularly placed within vasculature to thereby provide embolic protection. Such devices are often implanted temporarily within vasculature and removed upon being satisfied that the undesirable embolic material has been captured.

In certain situations, it is desirable to aid the formation of thrombus. For example, devices may be placed within aneurysmal spaces to slow and eventually cease blood flow therethrough. This procedure is sometimes referred to as embolic therapy, the basic thrust of which is to minimize or eliminate exposure of weakened sections of vasculature to blood flow and pressure.

Unfortunately, many of the devices intraluminally inplanted into the vasculature or other body lumens of a patient may cause additional trauma to already injured blood vessels. Whether self-expanding or plastically deformable, stents characteristically have an open mesh construction, or are formed with multiple openings to facilitate radial expansion and reduction and to permit tissue ingrowth in and around the mesh structure. Conventional devices can lack a profile suited to avoid traumatic engagement with a vessel wall. The wire ends of the mesh or braided structure may be sharp and hard and may cause trauma to the vessel wall. In addition, the ends as well as the intersections or crossings of the mesh or braided structure may attract blood platelets and therefore, cause thrombosis.

Additionally, certain of conventional mesh or braided structures can lack sufficient structural integrity for a particular purpose. That is, members defining the mesh or braided structures can be translated in response to a load which thereby minimizes the effectiveness of the repair devices. Accordingly, in such applications, structures having higher structural strength may be desirable.

Hence, those concerned with repair of diseased vasculature or other body lumens have recognized the need for devices that can be employed to retain the patency of a lumen or otherwise effectively repair the lumen without causing additional trauma. The present invention fulfills these needs.

SUMMARY OF THE INVENTION

Briefly, and in general terms, the present invention is directed towards devices contemplated for the repair or support of vasculature or other body lumens. Basically, the invention is directed to protector elements for use in combination with medical devices. In one aspect, the present invention includes a self-expanding, cyclindrical braided or mesh structure that is characterized by having protector elements either on the ends or at the junctions of the wire strut elements defining the braided or mesh structure, thereby presenting surfaces that are atraumatic to vessel walls or defining a structure with a streamlined profile and an enhanced structural integrity.

The structure of the present invention is referred to as a braid or a mesh. Braiding is the interlacing of wire sections at various angles to each other to form a braid. It is also within the scope of this invention to interweave or overlay strands of material, as in a mesh or a screen. It is to be recognized, however, that the disclosed protector elements can be used in combination with medical devices embodying various different types of structures not including a mesh or braided pattern, such as a framework cut from a tube.

In one preferred embodiment, the devices of the present invention are fabricated from a self-expanding, cylindrical structure defined by strut elements forming a braid or mesh. The cylindrical braided or mesh structure is attached to a protector element in the form of graft ends or cuffs, employing a means for attachment, such as a suture that attaches the cuff to each end of the braided structure. The cuff may cover the end of the braided or mesh structure by encasing it in an annular space forming a channel or shelf around the inner and outer surfaces of the end of the braid or mesh. The cuff may also be attached inside of the braid end, forming a single layer. Either as a double layer or as a single layer, the cuff presents a surface that is atraumatic to vessel walls. In one preferred embodiment, a woven polyester graft is used with a 3-OT polyester suture to attach the graft to a braided stent. Alternatively, the end or cuff may be made of plastic.

It is common procedure following the deployment of a braided or mesh structure to either move a balloon catheter or other components of a delivery system distally from the proximal end of the braid or mesh or insert a catheter or an angiocatheter from the distal end of the braid or mesh. During this procedure, it has been noted that the braided wire ends in a conventional structure may interfere with the devices being inserted. The graft ends or cuffs of the invention serve to keep the wire ends away from the lumen so that the ends do not interfere with the catheter or other devices placed through the lumen of the braided structure.

In addition, by adding a cuff to the ends of a braided structure, the potential inward bending of the braided or mesh wire ends noted in conventional structures may be prevented. If the cuff is attached inside of the braid end, forming a single layer on the inside, the exposedbraid wires on the outside may still function to facilitate adhesion to the vessel. The exposed wires may also provide the radial force and the structural support if the braid is placed inside a cuff where there is less of a concern with interference with medical devices placed through the braid.

In another preferred embodiment, the braided or mesh structure composed of strut wires has protector members or shoes attached to the ends or junctions of the adjacent strut wires. In another aspect of the invention, the protector members or shoes connect or secure the intersecting or adjacent wires of the device. The protector members or shoes serve to protect the junctions of the strut wires, maintain the structural integrity of the device, and present a surface that is atraumatic to vessel walls.

In one embodiment, the protector members or shoes may be made of plastic. In another embodiment, the protector members or shoes may be made of metal or other materials.

The disclosed self-expanding, braid or mesh devices with graft ends, cuffs, or other protector members are intended for use in addressing various maladies affecting vasculature. In particular, the self-expanding, braided or mesh devices with protector members can be configured specifically to facilitate the repair of aneurysms and stenoses.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1:
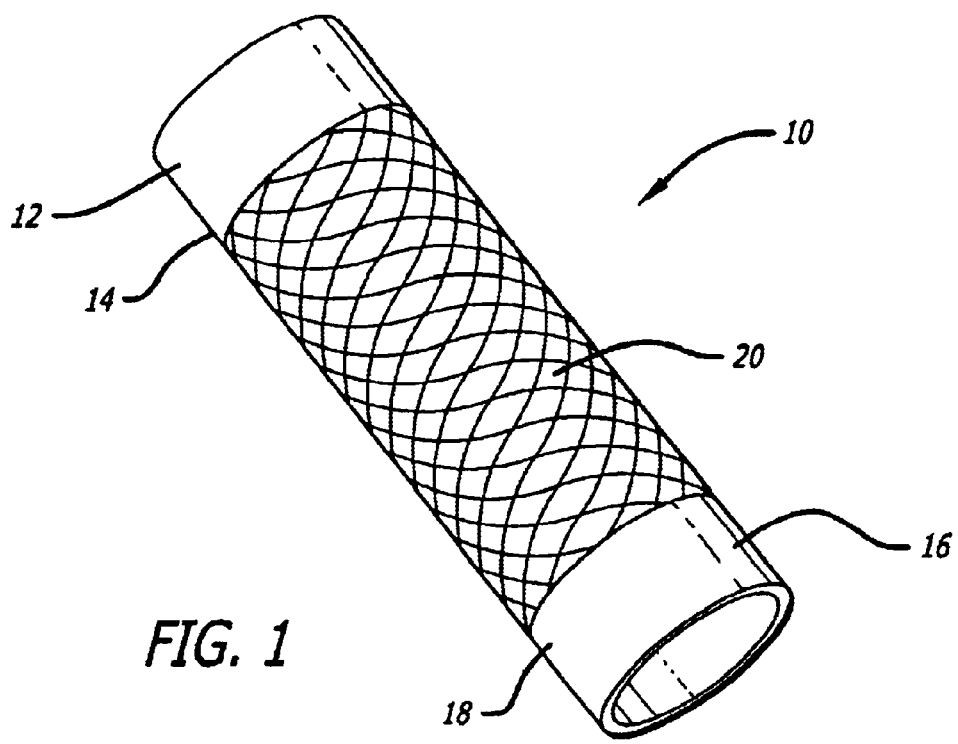
FIG. 1 is a perspective view of the braided or mesh device with end cuffs of the present invention.

As shown in the drawings, which were included for purposes of illustration and not by way of limitation, the present invention is directed towards protector elements for medical devices and in particular, for graft or stent devices. Although the protector elements are shown in combination with a braided or mesh type of medical device, the same can be used to provide various other types of medical devices with a atraumatic surfaces or well-defined intersection or converging members to thereby define a device with a desirable profile.

With reference to FIG. 1, there is shown a medical device 10 equipped with a first cuff 12 attached to a first terminal end portion 14 and a second cuff 16 attached to a second terminal end portion 18. As stated, the medical device 10 can assume a myriad of forms and can, for example, define a bifurcated or trifurcated configuration as well as tubular shape. The cuffs 12, 16 provide the medical device 10 with atraumatic ends which operate to minimize damage to body lumens or other areas in which the medical device is used in a patient. The cuffs 12, 16 can also provide the medical device with a profile well suited for receiving auxilliary components therethrough.

In a preferred embodiment, the medical device 10 is defined by a body 20 having a braided or mesh structure. In the conventional devices employing a braided or mesh structure, the ends 24 of the wire or elongate elements 28 (see FIG. 2, for example) used to create such structures are often left exposed. When implanting these conventional structures within a patient, for example, within vasculature, the exposed ends are left to directly engage walls defining vasculature or are otherwise left to interfere with blood flow or other medical devices used at the repair site. Consequently, the exposed ends can cause damage to tissue during implantation, repositioning, or after implantation during the natural movement of the tissue. That is, when used in vasculature, for example, pulsation of a vessel in response to the blood flow can cause the exposed ends to injure the vessel. Also, when used in vasculature, easy access through a lumen defined by the medical device may be required so that the guidewires or balloon catheters can be advanced therethrough. To wit, medical devices embodying sharp end portions or other structures projecting radially inwardly can act as an obstruction.

Figure 2:
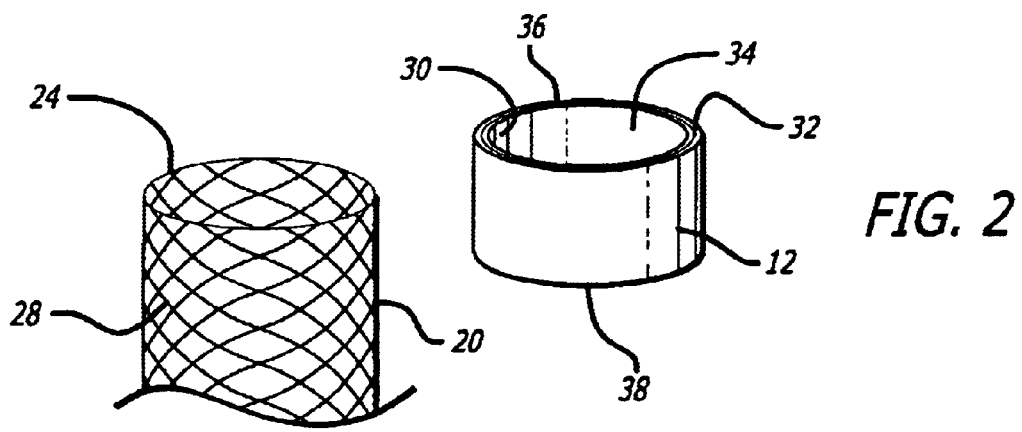
FIG. 2 is an exploded view of the assembly shown in FIG. 1.
Figure 3:
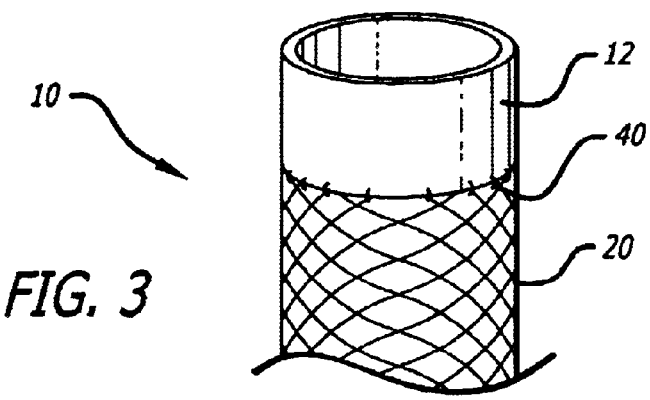
FIG. 3 is a partial perspective view of the components shown in FIG. 2 in an assembled configuration.
Figure 4:
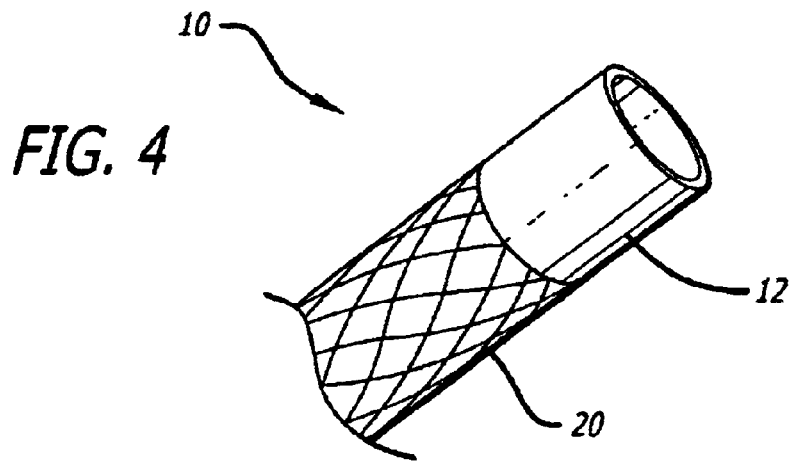
FIG. 4 is a partial view of the braided or mesh device with end cuffs secured by sutures to the braided or mesh device.

By equipping the medical device 10 with a cuff 12 as shown in FIGS. 2–4, the medical device 10 can be configured with atraumatic ends as well as a profile well suited for receiving additional medical device therethrough. In one aspect, the cuff 12 is generally cylindrical and includes an internal bore 30. The cuff additionally includes an annular space 32 for receiving an end portion 24 of a body 20 of the medical device 10 of the present invention. An entrance 34 to the annular space is provided at a first end 36 of the cuff 12. In a preferred embodiment, the second end 38 is closed to thereby define an annular space 32 having a blind end.

In one embodiment, the cuff 12 is made from flexible materials such as the materials used for conventional woven grafts. That is, it has been found that cuffs made from PTFE or PE or equivalent materials are acceptable for providing the cuff with the desired profile. The cuff 12 can be attached to the body 20 of the medical device 10 by employing sutures 40, though any structures or means for attaching the cuff 12 to a medical device 10 is acceptable. Moreover, the cuff 12 can be configured to receive a portion of the body 20 and to engage both an interior and an exterior segment of the body.

By utilizing a cuff 12 with an annular space 32, the ends 24 of a medical device 10 can be made to be atraumatic. Also, the wires or elongate or other structures at the end of the medical device 10 can be contained so that easy delivery of the device as well as insertion of the delivery components or other medical devices thereafter is facilitated. Moreover, equipping the medical device 10 with the contemplated flexible cuffs 12, 16, the assembly can be conveniently configured to assume a compressed form for transportation through and delivery within body lumen such as vasculature (see FIG. 4). Thus, the medical device 10 can be compressed into a low profile and placed within or on a delivery catheter (not shown) so that the device can both be advanced through tortuous and small diameter spaces thereby making the device useful in various areas of the patient's body.

Figure 5:
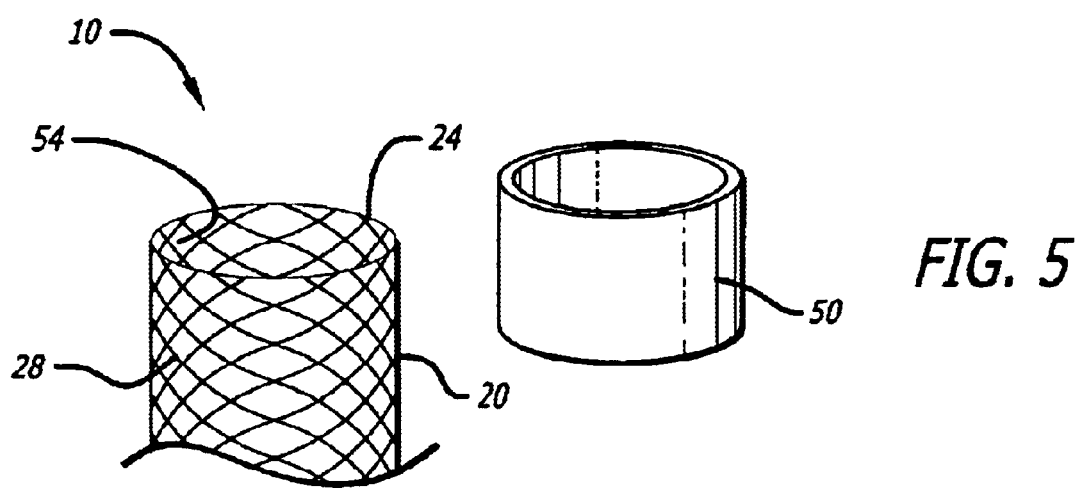
FIG. 5 is an exploded view depicting a braided or mesh device and an alternative embodiment of an end cuff.
Figure 6:
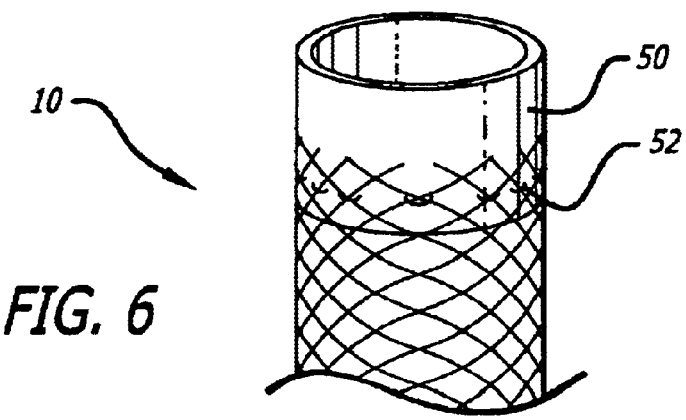
FIG. 6 is a partial perspective view depicting the components shown in FIG. 5 in an assembled configuration.
Figure 7:
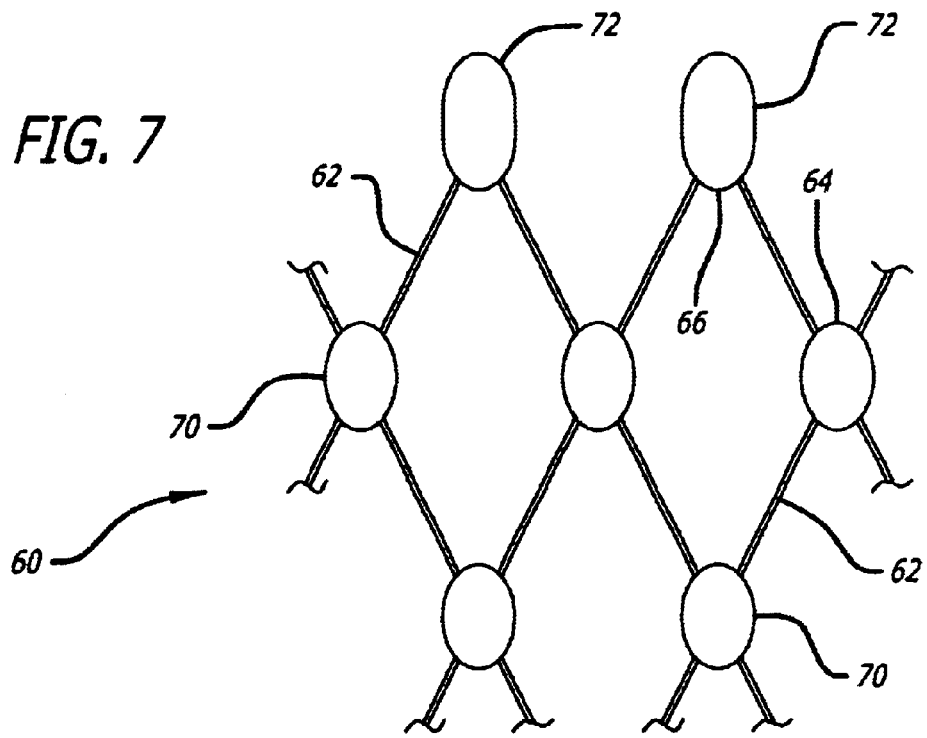
FIG. 7 is an enlarged view of a portion of a braided or mesh device with protector members or shoes at junction points and intersections of wire struts of the braided or mesh device.
Figure 8:
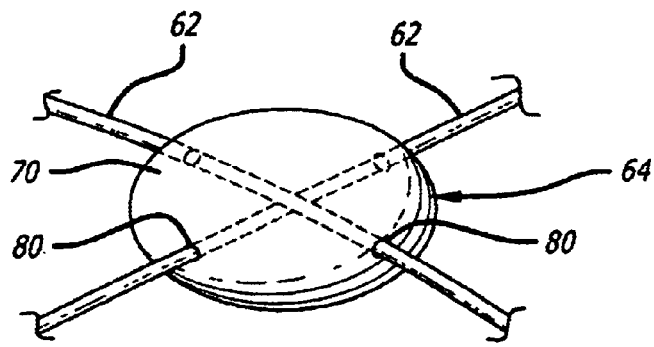
FIG. 8 is an enlarged side view of a protector member or shoe at an intersection of the wire struts medial ends of the braided or mesh device of FIG. 7.
Figure 9:
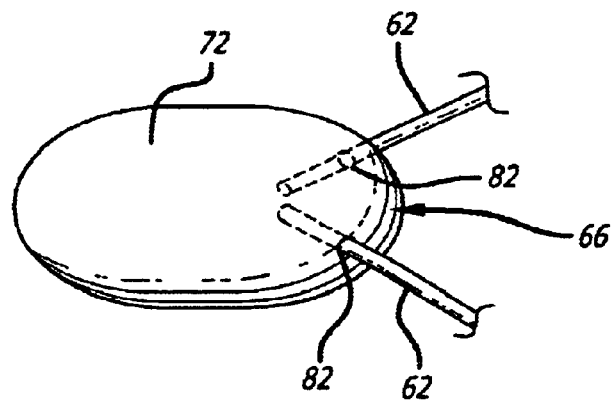
FIG. 9 is an enlarged side view of a protector member or shoe at an end junction point of wire struts of the braided or mesh device of FIG. 7.

In an alternative embodiment (see FIGS. 5 and 6), it is contemplated that the cuff 50 of the present invention lack an annular space and rather, defines a simple sleeve structure. Again, the cuff 50 can be formed from conventional graft materials and can be sutured or otherwise affixed 52 to ends 24 of the body 20 of a medical device 10. The cuff 50 can be attached to an internal bore 54 of the body 20 to provide the medical device 10 with a profile well-suited for receiving other medical devices. The ends 24 of the medical device 10 are then left to engage the tissue into which the medical device 10 is implanted and to provide a robust anchor thereto. It is also contemplated that the cuff 50 can be affixed to an external circumference of the body 20 of the medical device 10 (not shown) to provide the device with atraumatic ends where there is less of a concern for obstruction with other devices inserted through the medical device 10.

Turning now to FIGS. 7–10, there is shown a medical device 60 defined by intersecting or converging elongated members 62. At the intersecting or converging points 64, 66, there are boots or shoes 70, 72. A first boot or shoe 70 can define a generally elliptical sphere and includes a pair of through holes 80 spaced on an exterior surface of the boot 70. Each through hole 80 is adapted to receive an intersecting elongate member 62 and in combination, pairs of holes 80 operate to hold the members 62 in close proximity, but separated. The boot 70 can be designed so that the elongate members 62 freely slide therethrough or can be made to hold the members 62 in a fixed position relative to each other.

The boot 70 is contemplated to be made of any suitable biocompatible plastic and as such, can be molded or machined to specification. When the medical device 60 is in its assembled form, the boots or shoes 70 provide the device with structural integrity as well as provides atraumatic surfaces. Although the boots 70 are shown as being used with a braided or weaved medical device 60, it is contemplated that the same could be used in combination with any medical device requiring atraumatic surfaces or additional structural integrity.

Similarly, boots or shoes 72 can likewise be configured to receive converging elongate member 62 positioned at an end of a medical device 60. Such a boot 72 can be made from plastic and can be configured with blind end apertures 82 sized to receive elongate members 62 defining a medical device 60. It is contemplated that the boot or shoe 72 be affixed to the elongate members 62 to provide structural integrity as well as atraumatic ends. The affixation can be accomplished through the use of epoxies or an interference fit between the boot 72 and the elongate members 62.

Accordingly, the present invention provides medical devices that minimize trauma to body tissue. Additionally, the present invention provides medical devices with enhanced structural integrity and present a profile adapted for use with auxilliary medical devices.

While several particular forms of the invention have been illustrated and described, it will be apparent that various modifications can be made without departing from the spirit and scope of the invention. For example, references to materials are not intended to be limiting in any manner. Accordingly, it is not intended that the invention be limited, except as by the appended claims.

What is claimed is:

1. A medical device, comprising:
  a body portion having a first end portion and a second end portion and being defined by a structure including a plurality of pairs of converging struts;
  a first cuff, the first cuff being attached to the first end portion;
  a second cuff, the second cuff being attached to the second end portion;
  at least one shoe device, the shoe being configured at one pair of converging struts to maintain the struts in a spaced relationship; and
  wherein the first and second cuffs and the shoe device provide the medical device with atraumatic surfaces and a streamlined profile and wherein the shoe device permits the conveying struts to slide with respect of each other.

2. The device of claim 1, the first cuff further comprising an annular space.

3. The device of claim 2, wherein the first cuff is configured to receive a portion of the body portion and to engage both an interior and an exterior segment of the body portion.

4. The device of claim 1, the second cuff further comprising an annular space.

5. The device of claim 4, wherein the second cuff is configured to receive a portion of the body portion and to engage both an interior and an exterior segment of the body portion.

6. The device of claim 1, wherein the first cuff is configured to reside within an interior of the body portion.

7. The device of claim 1, wherein the second cuff is configured to reside within an interior of the body portion.

8. The device of claim 1, wherein the body portion is radially collapsible and the first and second cuffs cooperate to collapse with the body portion.

9. The device of claim 1, wherein the first and second cuffs are sutured to the body.

10. The device of claim 1, wherein the first and second cuffs are made from graft material.

11. The device of claim 10, wherein the graft material is PTFE.

12. The device of claim 10, wherein the graft material is PE.

13. The device of claim 1, wherein the shoe device provides the body portion with structural integrity.

14. The device of claim 1, wherein the shoe device if formed from a plastic material.

15. The device of claim 1, the shoe device further comprising a plurality of through holes which are sized to receive a section of strut.

16. The device of claim 15, wherein the plurality of through holes extend through a length of the shoe device.

17. The device of claim 1, further comprising a plurality of through holes, wherein the plurality of holes have blind ends.

18. The device of claim 1, wherein the shoe device is configured at converging struts located at a medial portion of the body portion.

19. A medical device, comprising:
  a body portion having a first end portion and a second end portion and being defined by a structure including a plurality of pairs of converging struts;
  a first cuff, the first cuff being attached to the first end portion;
  a second cuff, the second cuff being attached to the second end portion; and
  at least one shoe device, the shoe device being configured at one pair of converging struts to maintain the struts in a spaced relationship:
  wherein the first and second cuffs provide the medical device with atraumatic surfaces and a streamlined profile and wherein the shoe device permits the converging struts to slide with respect to each other.

* * * * *

UNITED STATES PATENT AND TRADEMARK OFFICE
CERTIFICATE OF CORRECTION

PATENT NO. : 6,786,919 B1
DATED : September 7, 2004
INVENTOR(S) : Arnold M. Escano and Shuji Uemura It is certified that error appears in the above-identified patent and that said Letters Patent is hereby corrected as shown below:

Column 3,
Line 5, delete "exposedbraid" and insert -- exposed braid --.

Column 6,
Line 3, delete "shoe being" and insert -- shoe device being --.

Signed and Sealed this

Fifteenth Day of February, 2005

JON W. DUDAS
*Director of the United States Patent and Trademark Office*